United States Patent [19]

Nelsen et al.

[11] Patent Number: 4,780,987

[45] Date of Patent: * Nov. 1, 1988

[54] METHOD FOR THE PREPARATION OF HYDRATED, PREGERMINATED SEEDS IN GEL CAPSULES

[75] Inventors: Charles Nelsen; Steven Strickland, both of Davis; Roxanne Davis, Sacramento; Keith Redenbaugh, Davis, all of Calif.

[73] Assignee: Plant Genetics, Inc., Davis, Calif.

[*] Notice: The portion of the term of this patent subsequent to Apr. 22, 2003 has been disclaimed.

[21] Appl. No.: 773,604

[22] Filed: Sep. 9, 1985

Related U.S. Application Data

[63] Continuation-in-part of Ser. No. 545,678, Oct. 25, 1983, Pat. No. 4,583,320.

[51] Int. Cl.$^4$ .................................................. A01C 1/06
[52] U.S. Cl. ..................................................... 47/57.6
[58] Field of Search ...................... 47/57.6, 58; 111/1, 111/6-7

[56] References Cited

U.S. PATENT DOCUMENTS

| | | | |
|---|---|---|---|
| 2,671,985 | 3/1954 | Vogelsang | 47/57.6 |
| 4,245,432 | 1/1981 | Dannelly | 47/57.6 |
| 4,251,952 | 2/1981 | Porter | 47/57.6 |
| 4,583,320 | 4/1986 | Redenbaugh | 47/57.6 |

Primary Examiner—Robert E. Bagwill
Attorney, Agent, or Firm—Limbach, Limbach & Sutton

[57] ABSTRACT

Novel methods are provided for the preparation and delivery of botanic seeds which are pregerminated and maintained in a hydrated state in gel capsules. Various types of botanic seeds are encapsulated, in some embodiments, with beneficial additives, in a gel matrix and pregerminated. These pregerminated seeds emerge more quickly than raw seeds from a number of planting matrices. These seeds can be encapsulated and pregerminated in variously described ways.

47 Claims, No Drawings

METHOD FOR THE PREPARATION OF HYDRATED, PREGERMINATED SEEDS IN GEL CAPSULES

This application is a continuation-in-part of our commonly assigned and copending application Ser. No. 545,678, filed on Oct. 25, 1983, now U.S. Pat. No. 4,583,320.

TECHNICAL FIELD

This invention relates generally to the field of agriculture and crop production and more specifically to the delivery of singulated, botanic seeds which are pregerminated (a.k.a. primed, vigorized, chitted) in a hydrated, polymer gel capsule to enable more rapid and uniform seedling emergence.

BACKGROUND OF THE INVENTION

Pregermination of botanic seed (a.k.a. priming, osmoconditioning, vigorizing, chitting) is a seed treatment by which early seed germination events up to, and sometimes including, radicle emergence are initiated under optimal conditions. The results of this pregermination treatment are that treated seeds often emerge more quickly and to a higher percentage than untreated or raw seeds under less than ideal environmental conditions (see M. Rivas, F. V. Sandstrom, and R. L. Edwards, "Germination and Crop Development of Hot Pepper after Seed Priming," HortScience, 19:279–281, 1984; D. J. Cantliffe, J. M. Fischer, and T. A. Nell, "Mechanism of Seed Priming in Circumventing Thermodormancy in Lettuce," Plant Physiology 75:290–294, 1984). According to several prior methods, after pregermination, the seeds are then either redried or planted immediately, usually under less than optimal environmental conditions. According to the instant invention, pregermination is accomplished in hydrated gel capsules, avoiding the shortcomings of prior art methods. The use of a capsule which contains sufficient free water to participate in the physiological processes of pregermination provides advantages over known methods of delivery.

At least two methods of delivering pregerminated seeds are known: hydration and redrying of raw seeds, and fluid drilling techniques. In the first method, seeds are hydrated in a solution of water alone, or water containing an osmoticum such as salt or polyethylene glycol for periods of time ranging from twenty-four hours to several days (see, A. A. Kahn, "Preconditioning, Germination and Performance of Seeds," p. 283–316, in "The Physiology and Biochemistry of Seed Dormancy and Germination," edited by A. A. Kahn, North-Holland Publishing Co., Amsterdam and N.Y. (1977)). After hydration but before radicle emergence, the seeds are removed from the pregermination solution and dried under various conditions. The pregerminated seeds are sown in the field or greenhouse in the same fashion as are untreated raw seeds. This method of pregermination and delivery has several drawbacks. First, the delicate hydrated seeds must be manipulated several times. This may lead to seed damage resulting in a reduced seed lot germination. This problem is greatly increased if any radicle emergence occurs prior to redrying. Secondly, the redrying process results in additional costs for increased handling, equipment, and energy inputs. Thirdly, the redrying process introduces the need for the primed seeds to be rehydrated when placed into any growth medium. This additional step could result in delayed emergence or increased susceptibility to soil pathogens.

The second previously known method for delivering pregerminated seeds is fluid drilling. In fluid drilling, seeds are first either pregerminated in water or an osmoticum as described above. Then, the seeds are added to a fluid drilling matrix such as Laponite in water or Agrigel in water. Finally, wet slurry of the seeds in a fluid drilling matrix is then delivered to the growing area. (See, D. Gray, "Fluid Drilling of Vegetable Seeds," Horticultural Reviews, p. 1–27, 1981). This method has at least three major drawbacks. First, the seeds are placed randomly in the fluid drilling matrix reducing the possibilities for precision planting. Secondly, the seeds are subject to handling after radicle emergence and root growth up to 1 to 2 cm which may result in increased root damage and loss of seedling viability. Thirdly, fluid drilling techniques require special equipment.

The basis for this invention lies in a method for providing for seed pregerminaton after encapsulation. This is accomplished by using a hydrated polymer gel as the encapsulant. The free water contained within the capsule is capable of participating in the pregermination process.

This unique method of pregermination in a gel capsule has the following advantages. It avoids the step of re-drying the seeds. Encapsulation in a hydrated polymer also allows singulation in a seed-sized capsule or pellet that can be precision drilled, eliminating one drawback of the fluid drilling method. Finally, encapsulation and pregermination can be controlled to prevent seed radicle emergence prior to planting. The instant technique also affords the possibility of safely handling the seeds, even after the radicle has emerged.

Additionally, this method of encapsulation and pregermination allows for the timely and effective delivery of a large number of useful additives which include but are not limited to fungicides, insecticides, nematicides, fertilizers, growth promoting agents, growth regulators and beneficial microorganisms, including but not limited to bacteria, fungi, nematodes, and actinomycetes.

Thus, an objective of this invention is to enable pregermination of botanic seeds in a hydrated, polymer gel capsule which results in more rapid and more uniform emergence of a greater percentage of seedlings from any growth medium.

Another objective of this invention is to enable the delivery of hydrated, pregerminated seeds to eliminate the need to dry and then to rehydrate the seeds in the growth medium.

A further objective of this invention is to provide singulated, pregerminated seeds to permit precision delivery of pregerminated seed to any growth medium.

A still further objective of this invention is to enable the delivery of pregerminated seeds in hydrated gel capsules along with a wide range of useful chemical and biological additives to further improve the performance of the seeds under a wide range of abiotic and biotic conditions.

A final objective of this invention is to control radicle emergence of pregerminated, hydrated seed, and also, to protect from damage any emerged radicles.

DISCLOSURE OF THE INVENTION

Methods and compositions are provided for the singulation, hydration and pregermination of botanic seeds within a gel capsule, in some embodiments, along with beneficial additives.

BEST MODE FOR CARRYING OUT THE INVENTION

Definitions

The terms "seed" or "botanic seed" will be used to mean any plant propagule which contains embryonic tissue which, under the appropriate conditions, will result in the growth and development of a plant body. These include zygotic seeds, parthenogenic seeds, somatic embryos, and other plant propagules such as potato seed pieces, beet seeds (fruits), cereal seeds (caryopses), etc., which will result in plant growth.

The term "pregermination" will be used in a generic sense to mean any method to begin the biochemical and physiological processes of seed germination before planting of the seeds. Other terms which are also used for this process include priming, osmoconditioning, vigorizing, chitting, etc.

In accordance with the invention, methods and compositions are provided for the hydration, addition of beneficial adjuvants and pregermination of botanic seed by encapsulation in a gel. Any botanic seed as defined in the definitions section has the potential to be pregerminated in a gel capsule.

Encapsulation Media—Gels

The seeds can be encapsulated in accordance with the present invention in any of numerous media which provide an appropriate encapsulation matrix, hereafter termed "gel". In general, a gel should allow embryo respiration by permitting diffusion of gases. The gel should provide a capsule strong enough to resist external abrasion and adverse forces, yet be pliable enough to allow the growth of the embryo and its germination at the appropriate time. It may be desirable to use various gels in combination, either as a mixture or in layers, to achieve the desired results. The gel selected should also be able to retain a considerable amount of "free water" which is able to participate in the physiological processes of pregermination. Free water should be available as 50–99.6% of the mass of the capsule, preferably 70–99.6% of the capsule mass.

Gels which have been found useful for encapsulating meristematic tissue include sodium alginate, guar gum, carrageenan with locust bean gum, and sodium alginate with gelatin. Other suitable gels include, but are not limited to:

TABLE 1. GEL AGENTS

I. Natural Polymers
  A. Ionic bonds (requires complexing agents)
    Alginate with Polypectate
    Sodium Pectate
    Furcellaran
    Pectin
    Hypnean
    Dextran
    Tamarind
    Guar Gum
    Gellan Gum
  B. Hydrophobic Interactions
    Amylose
    Agar
    Agarose
    Agar with Gelatin
    Gelatin
    Starch
    Amylopectin
    Cornhull Gum
    Starch Arabogalactan
    Gum Ghatti
    Gum Karagan
    Ti Gum
    Gum Tragacanth
    Wheat Gum
    Chitin
    Dextrin
II Chemically Modified Natural Polymers
  A. Ionic bonds (requires a complexing agent)
    Ethyl Succinylated Cellulose
    Succinylated Zein
    Carboxymethylcellulose
  B. Hydrophobic Interactions
    Methylcellulose
    Hydroxyethyl Cellulose
  C. Covalent Bonds
    Gelatin with Glutaraldehyde
III. Synthetic Polymers
  A. Covalent Bonds
    Polyacrylamide
  B. Hydrophobic Interactions
    Polyethylene Glycol
    Polyvinylpyrrolidone
    Polyoxyethylene
    Hydrophilic Urethane
    Polyvinylacetate
    Vinyl Resins
    Hydron (hydroxyethylmethacrylate)
    2-methyl-5-vinylpyridinemethylacrylate-methacrylic acid
  C. Ionic Bonds
    Sodium poly (styrene sulfonate) with poly (vinyl methyl pyridinium) chloride
    Sodium poly (styrene sulfonate) with poly (vinyl benzyl trimethyl ammonium) chloride
    Strongly acidic polyanion with strongly basic polycation
    Bordon Poly Co. ® (vinyl acetate homopolymer) (Bordon Co.)
    Gelvatol ® (polyvinyl alcohol resin) (Monsanto)
IV. Stabilizing Compounds
  A. Trade Names
    Super Slurper ® (USDA, SEA-AR, Nor. Reg. Res. Lab)
    Viterra ® (Union Carbide)
    Laponite ® (Laporte (United States) Inc.)
    Gelrite ® (Kelco)
    SeaKem ® (FMC Corporation)
    SeaPlaque ® (FMC Corporation)
    SeaPrep ® (FMC Corporation)
    IsoGel ® (FMC Corporation)
  B. Organic Compounds
    Methylan Clear Wallpaper Paste
    Lactose
    Protein Colloids

Selecting Optimum Gels

A gel chosen for encapsulation would usually include the following characteristics (although it will be recognized by those skilled in the art that the invention may be practiced in other modes):

1. A compliance adequate to protect and cushion the pregerminated seed;

2. The interior material would have solubility or emulsion forming characteristics such that it can accept and contain additives, including but not limited to aqueous, non-soluble, or hydrophobic substances;

3. An outer surface to provide a protective barrier to mechanical stress, facilitate handling, and maintain seed viability;

4. Sufficient gel strength to maintain capsule integrity, but still allow the radicles and roots to break out during germination and for the additives to be contained and released.

Selection of Additives

It has been recognized that plant establishment, growth, and development may be enhanced by addition of additives to the soil, to the rhizosphere of the plant, and to the surface of the plant. It has also been demonstrated that controlled release of the additives may provide additional enhancement to plant growth, e.g., T. J. Roseman and S. Z. Mansdorf, "Controlled Release Delivery Systems," (Marcel Dekker, Inc., N.Y., 1983).

Additives which have been found to be useful for encapsulation with pregerminated seeds include pesticides, fertilizers, energy sources, growth promoters, growth regulators, safeners, and microorganisms.

TABLE 2. ADDITIVES

I. Pesticides
  A. Fungicides
    Copper sulfate
    Thiram
    Captan
    Benomyl
    Metalaxyl
  B. Insecticides
    Carbofuran
    Acephate
    Malathion
  C. Herbicides
    Pronamide
    Ethyl dipropyl thiocarbamate
II. Fertilizers and Nutrients
  Nitrogen
  Phosphorus
  Potassium
  Sulfur
  Calcium
  Magnesium
  Amino acids
  Micronutrients
III. Energy sources
  Sugars
  Carbohydrates
  ATP
IV. Microorganisms
  Pseudomonas species
  *Bacillus thuringiensis*
  Mycorrhizal fungi
  Rhizobia species
  *Bacillus subtilis*
  Actinomycete species
V. Growth Regulators and Hormones
  Giberellic Acid
  Cytokinins
  Naphthalene acetic acid
  Indole acetic acid
VI. Other Biologically Active Components
  Denitrification inhibitors
  Iron chelators
  Pheromones
  Enzymes
  Pesticide Antidotes and Safeners
VII. Other Inert Components
  Soil and water conditioners
  Dispersants
  Wetting agents
  pH altering compounds

Encapsulation with Selected Gel

There are two methods by which gel capsules can be formed. In the first method, a sodium alginate solution, for example, will form a gel when the gel is added to a complexing agent. Calcium chloride ($CaCl_2$) is generally used, however, lanthanum chloride, ferric chloride, cobaltous chloride, calcium nitrate, calcium hydroxide and copper sulfate are also acceptable, as generally are other compounds with multivalent cations.

A chosen gel will have a range of concentrations usable in working the invention. A concentration should be chosen to optimize ease of handling, gelling time, strength of gel and coating thickness around the meristematic tissue.

The sodium alginate may be prepared in a concentration of 1 to 10% w(in grams)/v(in milliliters) in water, more usually 1.5 to 5% and ideally from 1.5 to 3%.

The seeds to be encapsulated may then be added to the sodium alginate solution at a concentration of 1 to 50 seeds per milliliter, more usually from 5 to 20 seeds per milliliter. This concentration will vary as the appropriate size of seed varies with species, source and stage of development.

The seeds can be singulated or dispersed in gel solution which is then added dropwise to the complexing agent. Alternatively, the gel solution and complexing agent may be mixed by any of numerous techniques known to the art. These may include droplet formation and agent addition as a one step process by a vibrating nozzle which ejects a gel droplet from one source and coats the droplet with complexing agent from another.

The calcium chloride (or other complexing agent) may be made up in solution at a concentration of 1 to 1,000 millimolar, more usually 20 to 500 millimolar and ideally from 50 to 100 millimolar. Other complexing agents will have different preferred concentration ranges.

The time for gel formation and the temperature of the gelling solutions are interrelated parameters, for selected concentrations of gel and complexing agent. The temperature should be chosen so as to avoid damage to the seed, usually in the range of 1° to 50° C., more usually 10° to 40° C., and preferably at 20° to 30° C.

Within the range of acceptable temperatures, a particular value may be chosen to give the shortest possible gelling time consistent with complete gel formation. Typically, the gel will form immediately, but the full complexation takes longer. For a solution of sodium alginate at a concentration of 2.0 grams per 100 milliliters $H_2O$, calcium chloride solution concentration of 100 millimolar and 25° C. reaction temperature, adequate gelling is obtained in 5 to 120 minutes, more often 10 to 90 minutes and is usually sufficiently complete in 20 to 30 minutes.

The gel characteristics described above are modifiable for each gel, but are determined generally by the concentration parameters and chemical properties of the gel.

In the second method for gel capsule formation, a complexing agent, applied to the seeds, will cause a gel to form around the seed when the seeds are added to the gel agent. Calcium chloride ($CaCl_2$) is an example of a complexing agent which can be applied to the seeds and will cause a polymerized gel capsule to form around the seeds when the seeds are introduced to a gel agent such as sodium alginate solution.

Furthermore, each seed, when treated with a complexing agent, becomes a nucleus for the gel polymerization reaction. When properly manipulated, this system of encapsulation results in singulation and centering of each seed within a capsule.

Calcium chloride ($CaCl_2$) is the complexing agent generally used, however, ferric chloride, calcium nitrate, superphosphate fertilizer, and pesticides such as benefin are also acceptable, as are other compounds generally with multivalent cations.

A chosen gel will have a range of concentrations usable in working the invention. A concentration should be chosen to optimize ease of handling, gelling time, strength of gel and coating thickness around the seed. If the gel is too concentrated, the solution may be too viscous to allow stirring and will therefore make it difficult to immerse the treated seed into the gel solution. The sodium alginate, for example, can be prepared in a concentration of 0.2 to 5% w(in grams)/v(in milliliters) in water, more usually 0.4 to 2.5% and preferably from 0.6 to 1%.

Specific additives to be encapsulated can then be added to the sodium alginate at concentrations specific for the application rates of the particular additives. Pesticides, for example, can be added to sodium alginate in concentrations up to 99.4% of the alginate solution. More usually, pesticide concentrations will be from 0.002 to 0.300 milliliters formulated pesticide ($2 \times 10^{-4}$ to 0.30 grams active ingredient) per milliliter Fertilizers, for example, can be added at a concentration of 0.1 to 1,000 milligrams per milliliter sodium alginate. Microorganisms, for example, can be added at a concentration of 1 to $10^{12}$ microorganisms per milliliter. Carbon sources can be added at a concentration of 1 to 500 milligrams per milliliter of sodium alginate solution, more usually 5 to 100 milligrams per milliliter.

The complexing agent-treated seeds can then be added to the dispersed additives in gel solution. Agitation of the gel solution is usually desired to enhance the rapid immersion of the treated seeds into the gel solution and to prevent clumping of the forming gel capsules.

The calcium chloride (or other complexing agent) can be made up in solution at a concentration of 0.05M to 6.2M or, a saturated or supersaturated solution), more usually 0.3M to 6.2M, and ideally from 0.6M to 2.0M. Other complexing agents will have different preferred concentration ranges. The seeds can then be treated with the calcium chloride (or other complexing agent) solution by soaking, spraying, dipping, pouring or any of several other methods which will deposit an amount of the complexing agent on the seeds. When soaking tomato seeds in $CaCl_2$ solution in preparation for performing the method, the time in solution may be from 1 second to 24 hours, more usually 1 minute to 1 hour, and ideally from 2 to 10 minutes. Alternatively, the $CaCl_2$ (or other complexing agent) may be added to the seeds in a solid form. Anhydrous $CaCl_2$, for example, may be applied to the seeds using sticking agents such as paraffin oil.

The time for gel formation and the temperature of the gelling solutions are interrelated parameters, for selected concentrations of gel and complexing agent. The temperature should be chosen so as to avoid damage to the seed, usually in the range of 1° to 50° C., more usually 10°0 to 40° C., and preferably at 20° to 30° C.

Within the range of acceptable temperatures, a particular value can be chosen to give the shortest possible gelling time consistent with complete gel formation. Typically, the gel will form immediately, but the full complexation takes longer. For a solution of sodium alginate at a concentration of 0.6 grams per 100 milliliters $H_2O$, calcium chloride solution concentration of 1M and room temperature (22° C.), adequate gelling is obtained in 5 to 120 minutes, more often 10 to 90 minutes, and is usually sufficiently complete in 15 to 20 minutes.

The gel characteristics described above are modifiable for each gel, but are determined generally by the concentration parameters and chemical properties of the gel.

This gel encapsulation procedure is designed to maintain a high level of free water within the capsule. The external surface of the capsule is formed by a chemical reaction between the gel and complexing agent. The interior of the capsule remains wet, having a water content in excess of fifty percent, preferably between seventy and ninety-nine and sixth-tenth percent. This water is immediately available to the seed tissue within the capsule, water imbibition constituting an important first step in pregermination.

Pregermination

After capsule formation, seed pregermination can be initiated in either one of 2 ways. Once encapsulated, seeds will immediately begin the process of imbibition and germination. In the first method of pregermination, this process is allowed to occur for a specific period of time from zero to 7 days, more often 1 to 4 days and usually 1 to 3 days. The temperature for the pregermination treatment should be within the physiological range for seed germination, generally between 10° and 30° C. and more commonly 15° to 25° C.

After the appropriate time period, an osmotic agent in an aqueous solution of sufficient concentration to inhibit root and shoot growth is diffused into the capsules. The osmotic agent must be of sufficiently small molecular weight such that it will diffuse into the gel capsule (and out upon planting). Osmotic agents with high molecular weights will cause the water to move out of the capsule and cause the capsule to shrink and collapse around the seeds. A typically useful but not exclusive osmotic agent is a monovalent salt. Many monovalent salts are useful, particularly those that can also serve as a plant fertilizer such as potassium nitrate ($KNO_3$). Potassium nitrate readily diffuses into gel capsules and inhibits germination at concentrations between 0.3 and 1.0 molar, more often 0.4 to 0.6 molar and usually 0.4 to 0.5 molar. The salt is diffused into the capsule by stirring a volume of capsules in a larger volume of salt solution for sufficient time. Stirring times for a 0.4 molar solution range from one to three hours and for a 0.5 molar solution from 0.5 to one hour, depending on seed type and capsule size. Small molecular weight organic molecules can also serve as an osmoticum. Mannitol at 0.6M to 1.4M will serve to control root emergence.

In the second method of pregermination, the osmotic agent is placed into the gel matrix and into the complexing agent (if one is required) before capsule formation. The presence of the osmotic agent from the time of capsule formation does not stop seed imbibition or the biochemical processes of germination, but does inhibit cell expansion (for example, Heydecker, W, and Coolbear, P., 1977, Seed Science and Technology 5: 353-425, see page 391). These capsules are then held at or near an optimal temperature for germination to begin for one to several days, depending on seed type. Both methods of pregermination succeed in obtaining faster emergence relative to raw seed from a soil matrix.

Experimental

In order to demonstrate the invention, the following experiments were carried out under a variety of conditions.

Example A

1. Pregermination of Tomato Seeds and Emergence from a Greenhouse Mix

Tomato seeds, variety UC82 (obtained from Garner Seed Co., Woodland, Calif.) were encapsulated using the first described method for encapsulation. Tomato seeds were placed singly, in a 2% alginate solution (2 grams LF-60 alginate in 100 ml $H_2O$) dropping from a separatory funnel and encapsulated by complexing the alginate in a 100 mM solution of $CaCl_2.2H_2O$. After storage for 3 days at 24° C., capsules were stirred for 3 hours in a 0.4 molar $KNO_3$ solution (1:4, capsule volume:salt solution). One hundred capsules and one hundred raw seeds were planted in a commercial greenhouse mix in a cool greenhouse and seedling emergence was monitored. Nine days after planting, 85% of the pregerminated encapsulated seeds had emerged, while none of the raw seeds had emerged. Fourteen days after planting, 98% of the pregerminated encapsulated seeds and 96% of the raw seeds had emerged. Similar results were found in a repeat experiment except only 92% of the raw seeds emerged.

2. Pregermination of Tomato Seeds and Emergence from Field Soil in the Greenhouse Non-sterilized field soil can contain numerous saprophytic and pathogenic microorganisms that can affect and reduce seed germination. An experiment similar to Example A.1. was performed except pregerminated, encapsulated seeds and raw seeds were planted in field soil in the greenhouse, rather than a greenhouse mix. Ten days after planting, 81% of the pregerminated, encapsulated seeds had emerged and none of the raw seeds had emerged. Twenty-five days after emergence, 90% of the seedlings from pregerminated, encapsulated seeds had emerged, while 45% of the raw seeds had emerged.

3. Timing of Pregermination Before $KNO_3$ Addition

Flexibility in the time of the addition of the germination controlling $KNO_3$ was tested. Seeds were encapsulated and pregerminated as described in Example A.2. except the $KNO_3$ was diffused into the capsules 1, 2, 3, or 4 days after encapsulation. One hundred capsules of each treatment and raw seed controls were then planted in field soil in the greenhouse, and emergence was monitored.

Time of first emergence was similar for all four treatments pregerminated in the capsule, and much ahead of raw seed emergence. All 4 pregermination treatments began emerging 5 days after planting and by day 10, emergence of the 1, 2, 3, and 4 day pregermination treatments had reached 87, 62, 80 and 74% emergence respectively. Raw seed emergence was 0 percent, 8 days after planting; 1% 10 days after planting; and did not reach 75% until 17 days after planting at which time the emergence of 1, 2, 3 and 4 day pregerminated seeds were 90, 67, 88 and 85% respectively (mean=82.5%).

4. Pregermination with Addition of $KNO_3$ at the Time of Capsule Formation

Pregermination in the capsule can also be achieved by adding the osmotic agent at the time of capsule formation as described in the second method for pregermination in gel capsules and holding the capsules at an appropriate temperature for one to several days. Tomato seeds were encapsulated as described in Example A.1. except 0.4M $KNO_3$ was included at the time of encapsulation. These capsules were held at 24° C. for 7 days. Additionally, seeds were encapsulated as described in Example A.1. for comparison. One hundred capsules of each treatment and 100 raw seeds were planted in a commercial greenhouse mix in the greenhouse and seedling emergence was monitored. On day 7 after planting, seedlings from 93% of the capsules with $KNO_3$ added at capsule formation had emerged, seedlings from 89% of the capsules with $KNO_3$ added 3 days after formation had emerged and only 8% of the seedlings from raw seeds had emerged. Emergence values at 14 days after planting (in the same order) were 95, 93, and 95%.

5. Field Emergence of Pregerminated, Encapsulated Tomato Seeds

Tomato seeds were encapsulated and pregerminated as described in Example A.1. One hundred capsules and one hundred raw seeds were planted in a field prepared in a manner similar to commercial, California tomato fields and emergence was monitored. Five days after planting and irrigation, 49% of the seedlings from the pregerminated, encapsulated seeds had emerged, while no raw seeds had emerged. Eighteen days after planting, 73% of the pregerminated, encapsulated seeds had emerged and only 56% of the raw seeds had emerged. This test was planted 5 times over 5 consecutive weeks with similar relative performance in all 5 tests.

6. Comparison of Pregerminated, Encapsulated Seeds with Pregerminated, Raw Seeds Raw seeds, which have been pregerminated and redried for handling, will often emerge faster than untreated, raw seeds. Pregerminated, encapsulated seeds will emerge even faster than pregerminated, raw seeds. Tomato seeds were pregerminated, and encapsulated as described in Example A.1. except the $KNO_3$ was added 2 days after capsule formation. Raw seeds were pregerminated by imbibing the seeds in an aerated 0.4M $KNO_3$ solution for 3 days (as described in the section labeled "Background of the Invention") then dried by exposing the drained seeds to room temperature air for 24 hours. One hundred of each of these two treatments and one hundred untreated, raw seeds were planted in the greenhouse in a commercial greenhouse mix and emergence was monitored. On Day 6 after planting, 31% of the pregerminated, encapsulated seeds had emerged, 3% of the pregerminated, dried raw seeds had emerged, and 0% of the untreated raw seeds had emerged. Final % emergence of all 3 treatments were similar (greater than 95%).

EXAMPLE B

1 Pregermination of Tomato Seeds in Capsules Formed Using the Second Encapsulation Method Tomato seeds were encapsulated as described above for the second encapsulation method. Tomato seeds were soaked in 1 molar $CaCl_2.2H_2O$ solution for 10 minutes, then dropped, singly into a stirring solution of 0.6% sodium alginate (0.6 grams LF-60 alginate in 100 milliliters of water). After 20 minutes, the capsules were sieved and washed with distilled water and pregerminated by holding for 2 days at 27° C. One hundred twenty-five of these and one hundred twenty-five raw seeds were planted in a cool greenhouse in field soil and emergence was monitored. Five days after planting, 31% of the pregerminated, encapsulated seeds had emerged and 10% of the raw seeds had emerged. Fourteen days after planting, both treatments had emerged to 59%.

EXAMPLE C

1. Pregermination of Tomato Seeds in the Presence of Agricultural Pesticides Tomato seeds were pregerminated and encapsulated as described in Example A.1. except the $KNO_3$ was added 2 days after capsule formation. One-half of the capsules included the fungicide metalaxyl (Ciba Geigy, Greensboro, N.C.) at a rate equivalent to recommended seed treatment rates (0.6 gm metalaxyl/kg seed=2.0 ug metalaxyl/capsule). Raw seeds were also treated with an equivalent rate of metalaxyl or left untreated as a check. One hundred sixty capsules or seeds of each of the 4 treatments were planted in autoclaved field soil.

Pregerminated, encapsulated seeds emerged more rapidly than raw seeds and the presence of the fungicide metalaxyl in the capsule did not affect emergence (Table 3).

TABLE 3
Emergence of Pregerminated, Encapsulated or Raw Seeds ± Metalaxyl

| Seed Treatment | Metalaxyl Concentration (gm/kg seed) | Emergence (%) Day 4 | Day 14 |
|---|---|---|---|
| pregerminated encapsulated seeds | 0 | 10 | 93 |
| pregerminated encapsulated seeds | 0.6 | 29 | 96 |
| raw seeds | 0 | 0 | 85 |
| raw seeds | 0.6 | 0 | 99 |

EXAMPLE D

1. Pregermination of Salvia in Gel Capsules

Samples of the ornamental flower seed Salvia (Park Seed, Greenwood, S.C., variety Hotline) were pregerminated and encapsulated as described for tomato in Example B except the $KNO_3$ was added immediately following capsule formation and capsules were held at 16° C. for 14 days. One hundred of the pregerminated, encapsulated seeds and one hundred raw seeds were planted in the greenhouse in a commercial greenhouse mix and emergence was monitored. Nine days after planting, 54% of the pregerminated, encapsulated seeds had emerged while only 17% of the raw seeds had emerged. By day 26 after planting, 73% of the pregerminated, encapsulated seeds had emerged and 74% of the raw seeds had emerged.

EXAMPLE E

1 Pregermination of Tobacco Seeds with Radicle Emergence in the Gel Capsule and Germination in a Greenhouse Mix Tobacco seeds (variety TR Madole) were encapsulated as described in Example A1, treated with 0.5M $KNO_3$ for 30 min 2 days after capsule formation and stored an additional 5 days at 24° C. Two days before planting, the salt was removed from ½ of the capsules by washing in deionized water for 1 hour to allow germination to occur. At planting (7 days after capsule formation) seeds in these capsules had undergone radicle emergence. Eighty each of capsules with radicle-emerged seeds, capsules with non-radicle-emerged seeds, and raw seeds were planted in a greenhouse mix in a cool greenhouse and seedling emergence was monitored. The encapsulation process protected the emerged radicles and these seeds emerged faster than did either of the other 2 treatments (Table 4).

TABLE 4
Emergence of Seedlings from Gel Capsules (± Radicles Emerged) and from Untreated, Raw Seeds

| Seed Treatment | Emergence Percentage | |
|---|---|---|
| | Day 9 | Day 22 |
| Pregerminated, Encapsulated Seeds with Radicle Emergence | 73.8 | 83.4 |
| Pregerminated, Encapsulated Seeds without Radicle Emergence | 46.3 | 80.0 |
| Untreated Raw Seeds | 0 | 67.5 |

We claim:

1. A method for preparation of singulated, hydrated, pregerminated seeds comprising the steps of:
    encapsulating in a capsule at least one ungerminated seed, said capsule formed from a hydrated, polymer gel;
    maintaining said seed capsules in a hydrated condition such that free water is available within the capsule to initiate seed germination;
    maintaining said seed capsules in conditions which permit germination;
    introducing osmotic growth inhibitor to said hydrated seed capsules; and,
    delivering said hydrated, pregerminated seed capsules to an environment for growth and development.

2. The method of claim 1 wherein said seed capsule contains between seventy and ninety-nine and six-tenths percent water by weight, from the encapsulation step until the delivery step.

3. The method of claim 1 wherein said step of maintaining seed capsules at germination conditions occurs from part of one day. to seven days.

4. The method of claim 1 wherein said osmotic growth inhibitor is characterized by low molecular weight.

5. The method of claim 1 wherein said seeds are members selected from the group consisting of zygotic seeds, parthenogenic seeds, and somatic embryos.

6. The method of claim 1 wherein said seeds are selected from the group consisting of potato seed pieces, beet seeds, and cereal seeds.

7. The method of claim 1 wherein said germination conditions comprise, in part, ambient temperatures between 10° C. and 40° C.

8. The method of claim 1 wherein said osmotic growth inhibitor is selected from the group consisting of sodium chloride, potassium nitrate and mannitol.

9. The method of claim 1 wherein, before the encapsulation step, there is an additional step of adding at least one beneficial adjuvant to a hydrated, polymer gel.

10. The method of claim 9 wherein said beneficial adjuvant is a member selected from the group consisting of copper sulfate, thiram, captan, benomyl, metalaxyl, carbofuran, acephate, malathion, pronamide and ethyl dipropyl thiocarbamate.

11. The method of claim 9 wherein said beneficial adjuvant is a member selected from the group consisting of nitrogen, phosphorus, potassium, sulfur, calcium, magnesium, amino acids and micronutrients.

12. The method of claim 9 wherein said beneficial adjuvant is a member selected from the group consisting of sugars, carbohydrates and adenosine triphosphate.

13. The method of claim 9 wherein said beneficial adjuvant is a member selected from the group consisting of Pseudomonas species, *Bacillus thuringiensis*, Mycorrhizal fungi, Rhizobia species, *Bacillus subtilis* and Actinomycete species.

14. The method of claim 9 wherein said beneficial adjuvant is a member selected from the group consisting of giberellic acid, cytokinins, naphthalene acetic acid, indolebutyric acid and indole acetic acid.

15. The method of claim 9 wherein said beneficial adjuvant is a member selected from the group consisting of denitrification inhibitors, iron chelators, pheromones, enzymes, pesticide antidotes and safeners.

16. The method of claim 9 wherein said beneficial adjuvant is a member selected from the group consisting of soil and water conditioners, dispersants, wetting agents and pH altering compounds.

17. A method for delivering singulated, pregerminated seeds to an environment for growth and development comprising the steps of:
encapsulating in a capsule at least one ungerminated seed, said capsule formed from a hydrated polymer gel containing osmotic growth inhibitor;
maintaining said seeds in a hydrated condition such that free water is available within the capsule to initiate seed germination;
maintaining said seed capsules at germination temperatures; and
delivering said hydrated, pregerminated seed capsules to an environment for growth and development.

18. The method of claim 17 wherein said seed capsule contains between seventy and ninety-nine and sixth-tenths percent water by weight from the encapsulation step until the delivery step.

19. The method of claim 17 wherein said step of encapsulating seed with osmotic growth inhibitor includes inhibiting cell expansion while allowing seed imbibation.

20. The method of claim 17 wherein said step of maintaining seed capsules at germination conditions occurs from part of one to seven days.

21. The method of claim 17 wherein said osmotic growth inhibitor is characterized by low molecular weight.

22. The method of claim 17 wherein said seeds are members selected from the group consisting of zygotic seeds, parthenogenic seeds, and somatic embryos.

23. The method of claim 17 wherein said seeds are members selected from the group consisting of potato seed pieces, beet seeds, and cereal seeds.

24. The method of claim 17 wherein said germination temperatures are between 10° C. and 40° C.

25. The method of claim 17 wherein said osmotic inhibitor is a member selected from the group consisting of sodium chloride, potassium nitrate and mannitol.

26. The method of claim 17 wherein, before the encapsulation step, there is an additional step of adding at least one beneficial adjuvant to a hydrated, polymer gel.

27. The method of claim 26 wherein said beneficial adjuvant is a member selected from the group consisting of copper sulfate, thiram, captan, benomyl, metalaxyl, carbofuran, acephate, malathion, pronamide and ethyl dipropyl thiocarbamate.

28. The method of claim 26 wherein said beneficial adjuvant is a member selected from the group consisting of nitrogen, phosphorus, potassium, sulfur, calcium, magnesium, amino acids and micronutrients.

29. The method of claim 26 wherein said beneficial adjuvant is a member selected from the group consisting of sugars, carbohydrates and adenosine triphosphate.

30. The method of claim 26 wherein said beneficial adjuvant is a member selected from the group consisting of Pseudomonas species, *Bacillus thuringiensis*, Mycorrhizal fungi, Rhizobia species, *Bacillus subtilis* and Actinomycete species.

31. The method of claim 26 wherein said beneficial adjuvant is a member selected from the group consisting of giberellic acid, cytokinins, naphthalene acetic acid, indolebutyric acid and indole acetic acid.

32. The method of claim 26 wherein said beneficial adjuvant is a member selected from the group consisting of denitrification inhibitors, iron chelators, pheromones, enzymes, pesticide antidotes and safeners.

33. The method of claim 26 wherein said beneficial adjuvant is a member selected from the group consisting of soil and water conditioners, dispersants, wetting agents and pH altering compounds.

34. Pregerminated seeds encapsulated in a hydrated polymer gel together with an osmotic growth inhibitor to form a seed capsule.

35. The seed capsule of claim 34 wherein said capsule contains between seventy and ninety-nine and six-tenths percent water by weight.

36. The seed capsule of claim 34 wherein said osmotic growth inhibitor is characterized by low molecular weight.

37. The seed capsule of claim 34 wherein said pregerminated seeds are members selected from the group consisting of zygotic seeds, parthenogenic seeds, and somatic embryos.

38. The seed capsule of claim 34 wherein said pregerminated seeds are selected from the group consisting of potato seed pieces, beet seeds and cereal seeds.

39. The seed capsule of claim 34 wherein said osmotic inhibitor is selected from the group consisting of sodium chloride, potassium nitrate and mannitol.

40. The seed capsule of claim 34 further comprising a beneficial adjuvant.

41. The seed capsule of claim 40 wherein said beneficial adjuvant is a member selected from the group consisting of copper sulfate, thiram, captan, benomyl, metalaxyl, carbofuran, acephate, malathion, pronamide and ethyl dipropyl thiocarbamate.

42. The seed capsule of claim 40 wherein said beneficial adjuvant is a member selected from the group consisting of nitrogen, phosphorus, potassium, sulfur, calcium, magnesium, amino acids and micronutrients.

43. The seed capsule of claim 40 wherein said beneficial adjuvant is a member selected from the group consisting of sugars, carbohydrates and adenosine triphosphate.

44. The seed capsule of claim 40 wherein said beneficial adjuvant is a member selected from the group consisting of Pseudomonas species, *Bacillus thuringiensis*, Mycorrhizal fungi, Rhizobia species, *Bacillus subtilis* and Actinomycete species.

45. The seed capsule of claim 40 wherein said beneficial adjuvant is a member selected from the group consisting of giberellic acid, cytokinins, naphthalene acetic acid, indolebutyric acid and indole acetic acid.

46. The seed capsule of claim 40 wherein said beneficial adjuvant is a member selected from the group consisting of denitrification inhibitors, iron chelators, pheromones, enzymes, pesticide antidotes and safeners.

47. The seed capsule of claim 40 wherein said beneficial adjuvant is a member selected from the group consisting of soil and water conditioners, dispersants, wetting agents and pH altering compounds.

* * * * *